United States Patent [19]

Næstoft et al.

[11] Patent Number: 5,071,433
[45] Date of Patent: Dec. 10, 1991

[54] BREAST PROSTHESIS AGGREGATE

[75] Inventors: Roland Næstoft, Allerod; Marianne S. Nielsen, Copenhagen; Niels Dreijer, Kokkedal, all of Denmark

[73] Assignee: Coloplast A/S, Denmark

[21] Appl. No.: 509,975

[22] Filed: Apr. 16, 1990

[30] Foreign Application Priority Data

Apr. 13, 1989 [DK] Denmark .............................. 1772/89

[51] Int. Cl.⁵ .............................................. A61F 2/52
[52] U.S. Cl. .......................................... 623/7; 623/8; 450/55
[58] Field of Search .................... 623/7, 8; 450/54, 55

[56] References Cited

U.S. PATENT DOCUMENTS 4,356,573 11/1982 Knoche .................................. 623/7
4,426,742 1/1984 Prahl ...................................... 623/7

FOREIGN PATENT DOCUMENTS 2742394 3/1979 Fed. Rep. of Germany .......... 623/7
2202745 10/1988 United Kingdom .................... 623/7

Primary Examiner—David J. Isabella
Assistant Examiner—Stephanie Iantorno
Attorney, Agent, or Firm—Ostrolenk, Faber, Gerb & Soffen

[57] ABSTRACT

A breast prosthesis aggregate consisting of (a) a flexible resilient breast prosthesis (10) imitating a female left or right breast; and (b) one or more flexible fastening slabs (12; 40,42) sealable to the skin of the wearer by a skin-friendly adhesive. The prosthesis can be releasably secured to the slab or slabs by complementary, interacting attachment members, preferably of the hook-and-loop type with the hooks on the prosthesis, placed on a backward ledge (18) on the prosthesis and the front side of the slabs. On the ledge the attachment members are arranged in separate areas (20) disposed at a mutual distance in an arched, upward convex pattern. Loop members of the closure may be placed in an analogous pattern or may cover the entire front side of the slab. Single slab (12) may be replaced by a number of small slabs (40,42) each corresponding to one area (20) of attachment members on the ledge.

13 Claims, 2 Drawing Sheets

BREAST PROSTHESIS AGGREGATE

The present invention relates to a breast prosthesis aggregate consisting of (a) a flexible, resilient breast prosthesis having a front imitating the shape of a natural female breast, and (b) one or more flexible fastening slabs having on the back side a skin-friendly adhesive adapted to adhere to the skin of the wearer in the area to fasten the prosthesis; the prosthesis is adapted to be releasably secured to the slab or slabs by means of complementary, interacting attachment members placed on a backward ledge in the prosthesis and on the front side of the slab or slabs, respectively, and said ledge is delimited from the outer periphery of the prosthesis by a flap and a lip-like border area adapted to bear tightly against the skin of the wearer at least along the upper parts of the lip and to extend in use past any fastening slab secured to the wearer's skin in the area to be covered by the prosthesis.

Having to wear a breast prosthesis to imitate a breast which has been removed by mastectomy is in itself a psychic strain and the strain will become extremely heavy should the prosthesis give rise to physical discomfort, for instance in the skin, or if the prosthesis does not completely bear tightly against the skin with its border area, at least at the upper part thereof.

Breast prostheses frequently are held in place by means of brassieres but various devices are known for releasably attaching them directly or indirectly to the skin by means of an adhesive, in particular by means of so called skin barriers. The prosthesis itself is normally made from a silicone rubber because silicone rubbers are flexible and have a resiliency and a density which closely resemble those of a natural breast. The silicone rubber is normally enclosed in a tight cover of thin plastic foil material such as a polyurethane or polyethylene. By adhesive attachment this cover may cause problems because it can be torn by frequent mounting and removal. A breast prosthesis normally lasts one to two years. A skin barrier normally lasts from about 3 days up to about a week before it has to be changed, depending on the degree of transpiration etc. The lifetime of a breast prosthesis will therefore easily be above that of a hundred skin barriers. The thin cover normally used for such prostheses cannot possibly stand that many replacements of the adhesive; in fact, suitable skin barriers are difficult to remove from the cover of the breast prosthesis without tearing the cover into pieces. And if the sticky sheet material is adhered directly to the silicone rubber constituting the prosthesis, this will quickly be picked into pieces.

It is therefore desirable to provide a system for the adhesive attachment of a breast prosthesis to the skin in a manner so as to avoid damaging the cover of the prosthesis by frequent mounting and dismounting.

From a German patent application published as No. 742394 it is known to provide the back of breast prostheses with attaching members which cooperate with attaching members on adhesive tapes or an adhesive disc to be applied to the female body at the place of the prosthesis. The cooperating attaching means may for instance be snap fasteners; they may be an annular hook-and-loop fastener in which one part has a large number of small loops and the other part has small hooks engaging the loops; or they may be an annular spring lock in which the back of the prosthesis is provided with an annular groove with a projection having T-shaped cross section and adapted to engage a corresponding recess in an annular projection on the adhesive plate.

Some of the embodiments shown in this publication have an obliquely backward facing lip-like border which is intended to cover the attaching members and which will be suitable for bearing against the skin of the wearer.

Thus, this known breast prosthesis is adhered indirectly to parts of the skin placed directly above one another (seen in the upright position of the wearer). This may cause a sensation of inconvenience in the skin since it has been found that by far the majority of relative displacements of parts of the skin are vertical by movement of the arms. By such displacements, tensions will arise between adhesive sites above one another and the adhesive tapes or an adhesive disc will try to counteract the skin movements, leading to a tautening, unpleasant sensation; the back of the prosthesis is not movable relative to the adhesive tapes or disc and will contribute to the resistance of the adhesive against skin-movements.

Besides, it has been found that a fastening along the entire margin of the prosthesis tends to release the hold locally and, moreover, may cause discomfort because of the excretion of sweat. The local release of the hold will especially take place in the upper parts and may easily cause the prosthesis to "gape" along its upper edge, which according to experience gives rise to psychical problems and imposes very heavy limitations on the wearer as to choice of clothing.

A breast prosthesis known from European patent specification No. 54197 is placed on the skin of the wearer by the adhesion of a solid of revolution having a large adhesive area compared to the area of the back of the prosthesis. The prosthesis has a circular recess with a marginal profile corresponding to the margin of the solid of revolution. After having been positioned, the prosthesis can therefore easily turn relative to the skin, and because of the large area of adhesive the same tensions as mentioned above may arise with consequent discomfort to the skin.

In practice the solid of revolution has to be rather rigid in order to keep the prosthesis in place and therefore it easily loses some of the adhesive connection to the skin. The risk therefore arises that the "gap" mentioned above between the upper part of the prosthesis and the skin will occur, and even in case of an intact sealing such gaps may occur unless the width of the solid of revolution is almost as great as the height of the prosthesis (the distance from the upper to the lower edge thereof).

It is the object of this invention to remedy the disadvantages mentioned and to provide a breast prosthesis aggregate which reduces the sensations of tension and other sensations of discomfort in the skin to a minimum, and which has very little or no tendency to losing the connection with the skin, especially along the upper edge of the prosthesis.

This is achieved according to the invention thereby that the ledge bears a number of attachment members disposed at a mutual distance in an arched, upwards convex pattern adapted to interact with attachment members present on the fastening slab or slabs on the skin opposite them, said ledge in its entirety being positioned at a distance of at least 5 mm plus the total thickness of the interacting attachment members in their locked position from a base surface defined by the periphery of the lip-like border area.

Since the slab or slabs, which are normally produced from a known skin barrier and are flexible, the tensions of the skin mentioned above will not cause discomfort because each slab is following them and because each of the attachment members is so small that it will not significantly hamper the movements of the skin, whereby the tensions will be avoided or at least minimized. Since moreover the attachment members on the back of the prosthesis are correspondingly small, and since the prosthesis (the silicone rubber) is also resilient at least to some degree, the prosthesis will also be able to follow the stretch movements between the individual attachment members on the prosthesis and thereby counteract discomfort due to stretch in the skin areas. Large prostheses, due to the amount of material used, may be hampered in their stretch movements between the individual attachment members; this is easily counteracted by partly hollowing the prosthesis and adapting its wall thickness to facilitate a relative resilient movement between the individual parts of the ledge. In other words, a recess or cavity may according to the invention extend from the ledge towards the front of the prosthesis.

The prosthesis according to the invention is made of a material known for the purpose, notably a silicone rubber with a thin cover of, e.g., a polyurethane or polyethylene. The fastening means may be one comparatively large slab or a number of smaller slabs, e.g. each corresponding to one area of attachment members at the ledge. The slab or slabs have to be flexible so as to be able to follow the movements of the skin. The adhesive part is for instance 1 to 3 mm thick, in practice often 1.1 mm thick. The adhesive expediently has the ability to absorb water and aqueous fluids. Thereby it can absorb sweat.

Several such skin barrier materials are commercially available; they are, i.a., developed to fasten body-worn devices to the body, e.g. ostomy bags to the skin around an ostomy opening. In the present case it is preferred to use the skin barrier material which is marketed, i.a. as sheets, under the registered trademark CURAGARD; it is described, e.g., in U.S. Pat. specification No. 4,376,732. It consists of a gel-like, resilient, adhesive material which is a mixture of (I) a continuous phase of (a) at least one physically cross-linked elastomer, preferably a styrene-isoprene-styrene block copolymer, (b) at least one tackifier resin in the form of a polymer or copolymer of for instance cyclopentadiene or pinene, (c) a plasticizer for the elastomer and optionally an oily extender; and (II) a discontinuous phase of at least one hydrocolloid which is swellable in water and is evenly dispersed in the continuous phase. The adhesive at one face has an elastic, non-adhesive water-impervious film, e.g. consisting of a polyurethane, and on its back (the side to be adhered to the skin) a detachable protective cover of for instance silicone treated paper. In practice such a skin barrier may be used for up to a week after which it has to be changed, i.a. because of absorption of sweat.

However, also various other known single or double-faced adhesive sheets may be used; various brands are commercially available.

Especially CURAGARD brand barrier material is able to absorb moisture (sweat) but only to a limited degree; when this degree is exceeded the material becomes more or less liquid and will have to be replaced by a fresh skin barrier. This does not represent a disadvantage as the capability of absorbing moisture is an important quality in the material; for simple hygienic reasons this replacement is desirable.

On the film side (i.e. the front) of the skin barrier it has attaching members on the entire surface or parts thereof, applied by, e.g., sticking or hot melting and adapted to cooperate with attachment members on the back of the prosthesis. The attachment members are preferably the loop parts and the hook parts, respectively, of a hook-and-loop closure (a closure of the VELCRO ® type).

However, other sorts of attachment members may be applied. They may e.g. consist of a number of snap fasteners where the male part is preferably positioned on the prosthesis and the female part preferably on the slab or slabs spring lock members; hooks and eyes, where the hooks are preferably placed on the prosthesis and the eyes on the slab (slabs); sealing, separate parts (having less adhesive power than has the sealing agent of the basis plate) to cooperate with the non-adhesive front side of the slab; interacting magnetic sheets, e.g. consisting of a rubber-like or other polymer material in which a great number of magnetic powder particles have been incorporated and placed so that the sheets on the slab or slabs has a polarity opposite to that of the sheets placed on the prosthesis. A magnetic closure may also be attained by incorporating a number of small permanent magnets in the ledge of the prosthesis to cooperate with a number of thin sheets of magnetic metal, alloys or sheets as mentioned above attached to the slab or slabs.

To facilitate the understanding of the structure of the prosthesis the following designations will be partly used to identify relative orientations: parts and surfaces intended to face the wearer besides "back" will also be designated "proximal"; parts and surfaces intended to turn away from the wearer will be designated "front" and "distal". "Medial" are parts closest to sternum and "lateral" are the parts most distant from sternum when the prosthesis is in use. "Vertical" is parallel to sternum, "horizontal" perpendicular to sternum, "upper" and "lower" and "height" refer to the upright position of the wearer.

The prosthesis of the aggregate is preferably unsymmetrical, imitating a natural left or right breast (preferably symmetrical with each other about a vertical plane) whereby the prosthesis in projection on its base surface advantageously is a right-angled to obtuse-angled triangle having strongly rounded angles and straight to curved sides, the larger angle being turned upwards, at least the lower side being faintly curved and having in use a mainly horizontal chord and the shortest side of the triangle being adapted to be positioned medially in use. In such a case it is advantageous according to the invention if the prosthesis is adapted to be secured by means of one fastening slab which has the shape of an angle and has attachment members on its front side, whereas the attachment members on the prosthesis are positioned partly (a) in an arched to angled pattern on the upper part of the ledge and extend to approximately a line containing the point of gravity of the prosthesis on the base surface when the prosthesis is lying thereon, and (b) partly below said line near the lower portions of the lip adjacent the two lower angles. The areas of attachment members on the slab may expediently be placed in a pattern substantially corresponding to the pattern on the ledge, i.e. being complementary thereto when the slab is seen from the front and the prosthesis from the rear.

In this embodiment it is advantageous according to the invention if the ledge is oblique relative to the base surface and has its greatest distance therefrom at the upper part of the prosthesis.

According to the invention the ledge may expediently, at least in the upper portion of the prosthesis, be positioned at a distance from the base surface of at least 10 mm including the total thickness of the interacting attachment member in the locked position. Thereby there is ensured a high degree of certainty that the prosthesis will not gape at its upper edge.

To reduce the weight of the prosthesis and augment its flexibility and resiliency it may according to the invention have a recess or cavity extending from its ledge towards its front. In order to give a pleasant feeling in the skin adjacent the slab or slabs, the inner surface of the lip may be coated with a soft textile material. Preferably this is a non-woven textile.

When the interacting attachment members are of the hook-and-loop type the areas of hooks will normally be placed on the ledge of the prosthesis and the loops on the slab or slabs. When there is only one slab, the areas of loops may according to the invention expediently be arranged in a pattern complementarily corresponding to the pattern of the hook areas on the ledge as defined hereinbefore. This is especially the case when the areas of hooks and especially the areas of loops are cut from commercial sheets thereof.

However, it is well possible to replace the commercial loop material produced to match the commercial hook material by some knit or woven textile material, e.g. flannel. If this is done, it is for reasons of ease of manufacture preferable that the slab, when only one, has loops, i.e. the textile material, on its entire front side.

Such a slab may merely consist of a suitably shaped piece of CURAGARD brand barrier material having the textile adhesively bonded to the front side.

Instead of a single slab it is also possible to use a number of smaller slabs which are attached to the skin by the wearer herself, especially when the interacting attachment members are of the hook-and-loop type. In that case each slab has an area as or slightly larger than an area of hooks on the ledge and has the loops on at least a part of the front. When intended to be used with a plurality of small slabs, it may be expedient that the areas of hooks on the prosthesis are of a uniform shape and size so as to facilitate the positioning of the slabs on the skin.

By arranging the patterns of the attachment members on the prosthesis as described there is obtained a great security that along the upper part they will nestle closely to the body of the wearer without "gap" during various movements of the body. The tight bearing to the body along the lower part and the sides rarely causes problems, will rarely be noticed, especially not by the wearer herself, and as a rule will be attained merely by the weight of the prosthesis. As the slab or slabs will not normally extend to the lower part of the prosthesis, it is further attained that it or they will irritate the skin only in the least possible area, and that discomforts in the skin notably during vigorous movements of the arms and the body will practically not occur.

BRIEF DESCRIPTION OF THE DRAWINGS

In the following the invention will be described more fully with reference to the drawings in which.

DETAILED DESCRIPTION OF THE PREFERRED EMBODIMENTS

The Figures are shown largely in a natural size (FIGS. 5-8 a bit oversized) but for the sake of clearness the thickness dimensions of the attachment members are exaggerated. In all of the Figures the attachment members are of the hook-and-loop type but it will be understood that any other attachment devices as mentioned hereinbefore may be used.

A prosthesis 10 (FIG. 1) is made of a well-known kind of material suited for the purpose, viz. a silicone rubber with an appropriate density and consistency to imitate a natural breast. It is flexible and to a certain degree resiliently extensible in the various spatial directions. The silicone rubber is covered with a closely fitting cover of a thin plastic foil, e.g. polyethylene or as in the embodiment shown a polyurethane. The primary purpose of the foil is to prevent the mechanically weak silicone rubber from being torn apart. The prosthesis might as well be made of a system of small cells filled with a liquid.

The prosthesis 10 is adapted to be detachably attached to the body of the wearer by means of a slab 12 (FIG. 3) provided with a skin-friendly, i.e. hypoallergenic or preferably non-allergenic adhesive barrier material, preferably CURAGARD brand barrier material as described hereinbefore, which adheres well to the skin and to a certain degree is capable of absorbing aqueous liquids (sweat).

In the embodiment shown the prosthesis can be releasably secured to the slab 12 by means of spaced apart attachment members 20 here in the form of small areas of hook parts of hook-and-loop closures, positioned on the prosthesis. In each such area a great number of small elastic hooks are placed on a textile-like or plastics material. Loop part attachment members 34 are located on the slab 12. The members 34 consist of a textile-like material having a great number of loops to which the hooks can engage, and are attached to a tightly woven support or layer of plastic sheet material.

Figure 1:
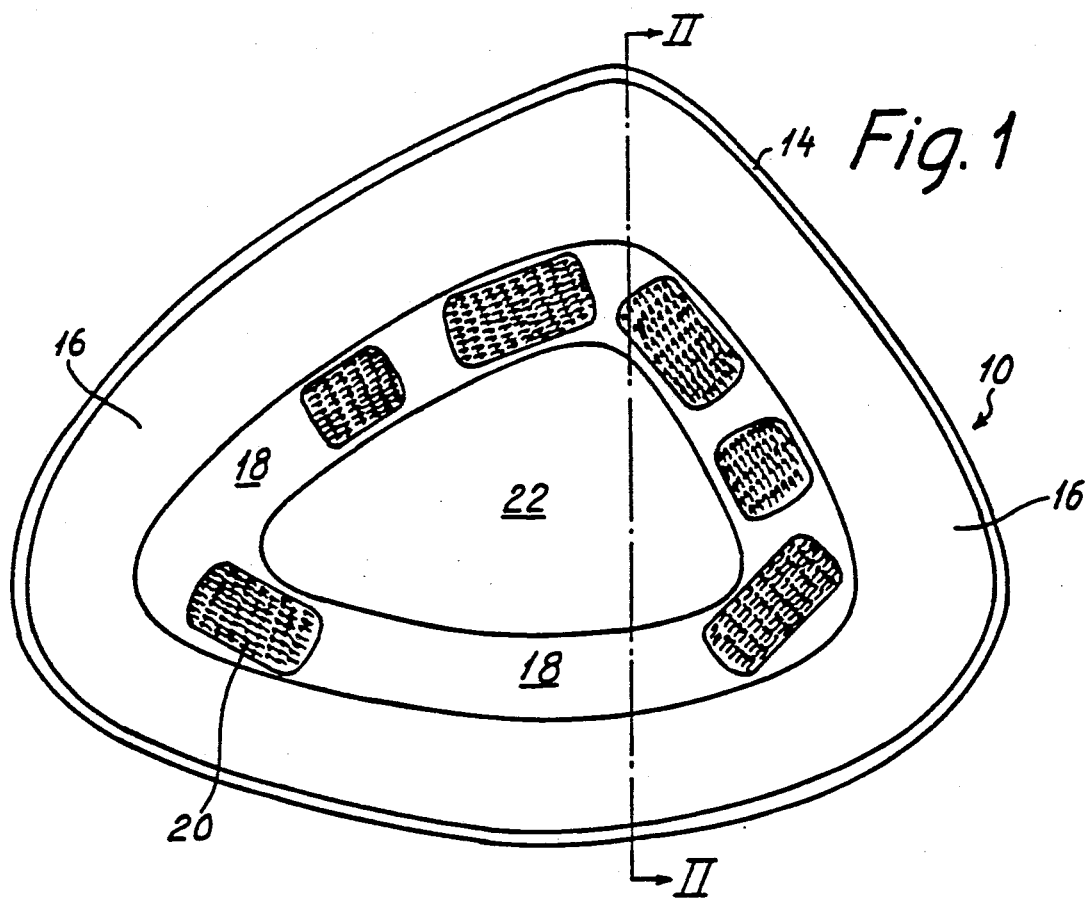
FIG. 1 is a plan view of the back of an embodiment of a breast prosthesis for a left breast belonging to the aggregate according to the invention.
Figure 2:
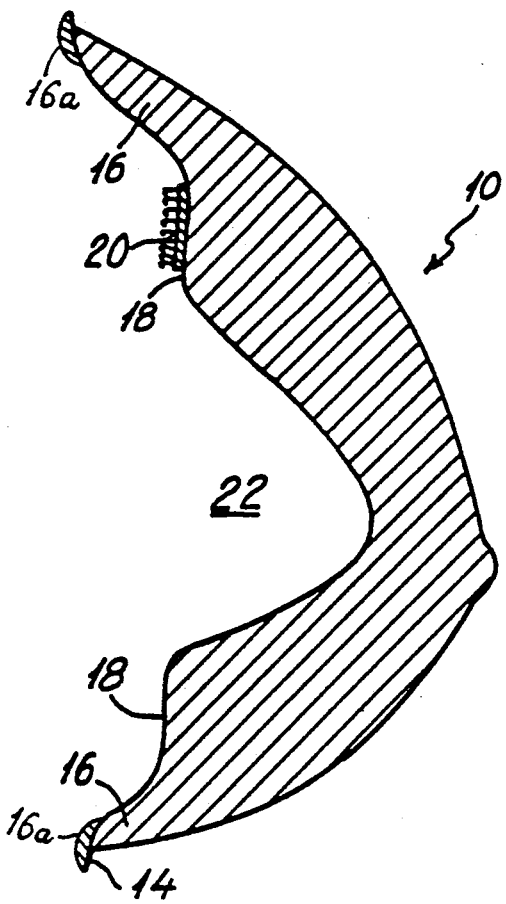
FIG. 2 is a section along line II—II in FIG. 1.
Figure 5:
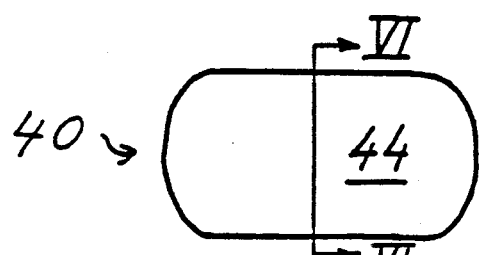
FIG. 5 is a plan front view of a small slab corresponding to a single area of attachment members on the prosthesis.
Figure 6:
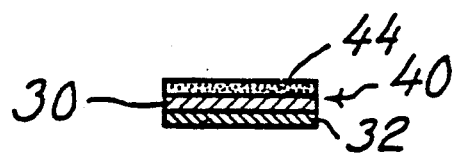
FIG. 6 is a section along line VI—VI in FIG. 5.
Figure 7:
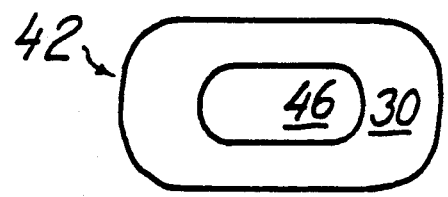
FIG. 7 is plan front view as similar to FIG. 5, but of another embodiment of the small slab.
Figure 8:
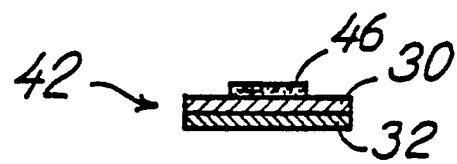
FIG. 8 is a section along line VIII—VIII in FIG. 7.

The breast prosthesis 10 seen from the back (the proximal side) in FIGS. 1-2 is unsymmetrical and intended for the left side; a corresponding right breast prosthesis would be symmetrical thereto.

In projection the prosthesis 10 is shaped approximately as an obtuse-angled triangle with the obtuse angle turning upwards, all angles being rounded and the sides being faintly convex. At the edge of the prosthesis its polyurethane cover has been extended so as to form a narrow flap 14 consisting of two layers glued and/or welded together in order to prevent the cover from being torn adjacent the edge.

The peripheral base portion of the prosthesis 10 is a lip 16 constituting (except for the flap 14) the entire border area of the prosthesis. Lip 16 may include a soft textile coating preferably of a non-woven textile. The prosthesis may have a vent, not shown, to interchange air between that part of the body covered by the prosthesis and surroundings without provoking unpleasant sounds. The vent is preferably placed in the laterally outermost part of the prosthesis.

The lip 16 is adapted to bear tightly in its entirety against the skin of the wearer, especially along the upper side of the prosthesis. This is attained partly by virtue of the flexibility of the prosthesis material and partly because the attachment members 20 are situated at a certain distance from a base surface defined by the outer periphery of the lip 16 (or flap 14). This base surface may be planar but is preferably faintly curved corresponding to the curvature of the human body in the sternum area.

The attachment members 20 (hooks) are, e.g. by sealing with a strong sealant, placed on a surface hereinafter called ledge 18, which in the embodiment shown is positioned approximately 15 mm from the above mentioned base surface in the upper part of the prosthesis and approximately 10 mm from there in the lower part of the prosthesis, see FIG. 2.

In the embodiment shown in FIGS. 1-2 the ledge 18 is annular, encircling a cavity 22, but especially in small prostheses it is preferably an uninterrupted plane surface so that the prosthesis is solid between the ledge and its front side. As shown in FIG. 2 the ledge may be oblique relative to said base surface but it may also be parallel thereto. The distance of the ledge from the base surface and hence the width of the lip 16 depends, i.a., on the size of the prosthesis and the kind of attachment members, but should ensure a certain pre-stressing of the lip when the attachment members are engaging each other. In the resting position of the prosthesis (not stressed, the attachment members not engaging each other) the distance of the ledge to the base surface must be at least 5 mm and, at least in the upper part, preferably at least 10 mm, in both cases plus the total thickness of the attachment members in their locked position The combination of the distance of the ledge from the base surface and the resiliency of the lip will ensure that there will occur no gap between the prosthesis and the body of the wearer during movements of the body and arms.

There are six of the attachment members 20, in the embodiment shown in FIG. 1. The members 20 are arranged at a mutual distance in an arcuate pattern on the ledge 18 near its transition into the lip 16; seen as a whole they are mainly parallel to the sides forming the obtuse angle. The distance between members may be only a few mm, but should preferably be at least 7 mm; thereby the ability of the prosthesis (the silicone rubber) to yield between the unelastic and non-stretchable (but bendable) pieces of hook-and-loop type closure will prevent unpleasant feelings of stretching and tension in the skin, e.g. due to vigorous upwards or backwards movements in the shoulder since, as explained below, the base plate is resiliently stretchable.

The number of attachment members 20 depends on the size and weight of the prosthesis and on the size of the members 20. When a hook-and-loop closure is used, the members 20 are preferably at most 2.8 cm long and 1.8 cm wide so as to allow for the necessary spacing especially at the upper part of a small prosthesis. A preferred size may be about 1.5×1.5 cm to about 1.5×2.5 cm. Horizontally placed closure members 20 may, however, have a length of up to 4 cm.

Figure 3:
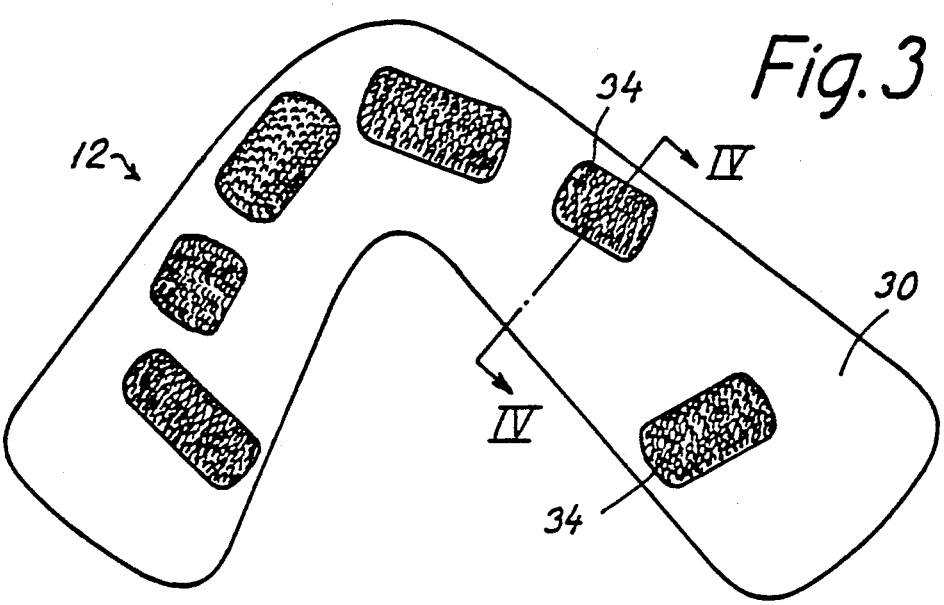
FIG. 3 is front elevational view of a slab for the prosthesis shown in FIGS. 1-2.
Figure 4:
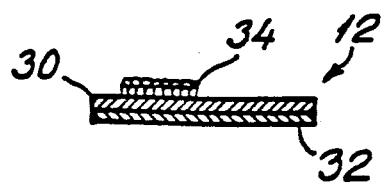
FIG. 4 is a section along line IV—IV in FIG. 3.

The slab 12 for attachment of the prosthesis shown in FIGS. 1-2 is shown from the front in FIG. 3 and in section in FIG. 4 (where the thickness is exaggerated relative to the other dimensions). It consists of a skin flange 30 having a detachable protective cover 32 on the back thereof and a number of loop members 34 on the front thereof. The skin flange 30 is preferably made from CURAGARD brand barrier material which is formed of substantially nonallergenic adhesive material and which has a very thin, elastic, non-adhesive water-impervious film (not shown). The skin flange may also be produced from another suitable, material. The loop members 34 are positioned in a pattern corresponding to the pattern on the prosthesis and have substantially the same size and the same spacing as the hook members 20. Optionally the hook members 20 and 34 may have different sizes to facilitate the application of the prosthesis. The skin flange 30 is somewhat bigger than necessary to accomodate the attachment members, viz. to ensure a sufficiently large sealing area.

The reason why the loop-part of the closure is subdivided into the individual members 34 especially is that the commercial variants of such closures, though bendable or flexible, are not really stretchable. In other words the subdivision into the members 34 has a function of avoiding the unpleasant sensations in the skin discussed hereinbefore. However, it is possible to replace the commercial loop parts of the hook-and-loop closure by a textile material which is able to engage the hooks. In that case the textile material may well occupy the entire front side of the slab 12 without any risk of discomfort to the wearer. Such a slab would have a similar cross section as that shown in FIG. 6.

It should be emphasized that the members 20 and 34 do not need to be rectangular as shown in FIGS. 1 and 3; they might as well be, e.g., elliptical or circular.

It is not necessary to have one slab only for fastening the prosthesis to the skin. Instead there may be a number of small slabs 40,42 as illustrated by FIGS. 5 to 8 (which are a little oversized relative to the other figures), the thickness dimension being exaggerated in FIGS. 6 and 8. Each small slab 40,42 corresponds to a hook member 20. The small slabs 40 and 42 are placed by the wearer in a pattern corresponding to that of the members 20. They are shown as being elliptical, which would be suitable for use for a prosthesis with members 20 as shown in FIG. 1, but it is obvious for those skilled in the art to decide which shape and size to select for use in combination with any given embodiment of a prosthesis made according to the present invention.

The small slab 40 is rectangular (with rounded angles) to elliptical and consists (see FIG. 6) of a piece of CURAGARD brand or other skin-barrier material provided at the back side with a protective cover 32 and at the entire front side with a layer of textile material 44, e.g. flannel, serving as the loop part of the hook-and-loop closure.

The small slab 42 has a similar shape but differs from the slab 40 in that a layer of textile material 46 does not cover the entire front side of the skin-barrier but only the middle part thereof. The areas of the skin-barrier not covered by the textile material are protected by an elastic, non-adhesive water-impervious film as referred to earlier. If the skin-barrier used is adhesive on both sides (ignoring the protective cover 32) the areas not covered by the textile material 46 may be protected by a protective cover similar to that on the back side.

Generally it is most expedient to place the hooks of the closure on the prosthesis and the loops on the slab or slabs in order to prevent the hooks from being caught in underwear or bed linen when the prosthesis is dismounted and the slab(s) remain on the body. If the prosthesis is very small and the distance between the slab(s) and the ledge 18 minimal, the hooks might cause discomfort by coming into contact with the skin. If so, the arrangement might be opposite but then it will be most expedient to protect the skin with a special plaster or to enlarge the total slab area.

The invention is not limited to the embodiments shown and described herein. The scope of the invention is defined by the following claims.

What is claimed is:

1. A breast prosthesis aggregate, comprising:
   (a) a flexible, resilient breast prosthesis having a front surface imitating the shape of a natural female breast and a back surface adapted to face a wearer, and
   (b) at least one flexible fastening slab having a back side, a front side, a skin-friendly adhesive located on the back side of the slab for adhering the slab to the skin of the wearer and at least one attachment member, located on the front side of the slab.
   wherein the prosthesis has attachment members which are complementary to and which are adapted to engage the at least one attachment member of the slab to releasably secured the prosthesis to the slab,
   wherein the prosthesis has a ledge formed in the back surface of the prosthesis, the attachment members of the prosthesis being located on the ledge,
   wherein the back surface of the prosthesis has a peripheral base portion adapted to bear tightly against the skin of the wearer at least along an upper part thereof and to extend in use past the fastening slab, the peripheral base portion being located between an outer periphery of the prosthesis and the ledge, the peripheral base portion having a base surface,
   wherein the attachment members of the prosthesis are disposed in a spaced relation in an arched, upwards convex pattern, and
   wherein said ledge in its entirety is positioned at a predetermined distance forward of the base surface, the predetermined distance being at least 5 mm plus a total thickness of the attachment members of the prosthesis and of the fastening slab when the prosthesis is secured to the slab.

2. An aggregate as claimed in claim 1, wherein the prosthesis is asymmetrical, the peripheral base portion being in the form of a triangle with a largest angle, two lower angles and a shortest side, the prosthesis being arranged such that in the use the largest angle is turned upwards and the shortest side is positioned medially.

3. An aggregate as claimed in claim 2, wherein the fastening slab is in the form of an angle.

4. An aggregate as claimed in claim 3, wherein the attachment members of the prosthesis include upper attachment members and lower attachment members, the upper attachment members being positioned in an arched or angled pattern on an upper part of the ledge, the pattern extending approximately to a line on the base surface which contains the center of gravity of the prosthesis, the lower attachment members being positioned below the line, near lower portions of the peripheral base portion and adjacent the two lower angles.

5. An aggregate as claimed in claim 1, wherein the ledge is oblique with respect to the base surface of the peripheral base portion.

6. An aggregate as claimed in claim 5, wherein an upper part of the ledge is positioned at a distance from the base surface which is at least 10 mm plus a total thickness of the attachment members of the prosthesis and of the fastening slab when the prosthesis is secured to the slab.

7. An aggregate as claimed in claim 1, further comprising a cavity formed in the back surface of the prosthesis extending from the ledge towards the front of the prosthesis.

8. An aggregate as claimed in claim 1, further comprising a coating of a soft textile material located on the base surface.

9. An aggregate as claimed in claim 8, wherein the textile material is nonwoven.

10. An aggregate as claimed in claim 1, wherein the attachment members of the prosthesis and of the slab are hook-and-loop devices.

11. An aggregate as claimed in claim 10, wherein the slab has a textile material on its entire front side.

12. An aggregate as claimed in claim 1, wherein the fastening slab has a plurality of attachment members.

13. An aggregate as claimed in claim 1, further comprising a second fastening slab with a second attachment member for releasably securing the prosthesis of the second attachment member.

* * * * *